(12) United States Patent
Liu et al.

(10) Patent No.: US 9,005,899 B2
(45) Date of Patent: Apr. 14, 2015

(54) CHITIN-INDUCED IMMUNE RESPONSE BASED METHOD FOR DIAGNOSING ALLERGIC ASTHMA IN PATIENTS

(75) Inventors: Chao-Lin Liu, Taipei (TW); Chia-Rui Shen, Gueishan Township, Taoyuan County (TW); Li-Chen Chen, Jhonghe (TW)

(73) Assignee: Mingchi University of Technology, Taipei Hsien (TW)

( * ) Notice: Subject to any disclaimer, the term of this patent is extended or adjusted under 35 U.S.C. 154(b) by 738 days.

(21) Appl. No.: 12/752,341

(22) Filed: Apr. 1, 2010

(65) Prior Publication Data

US 2011/0244488 A1 Oct. 6, 2011

(51) Int. Cl.
G01N 33/00 (2006.01)
G01N 33/53 (2006.01)
G01N 33/68 (2006.01)

(52) U.S. Cl.
CPC ........ *G01N 33/6893* (2013.01); *G01N 2333/57* (2013.01); *G01N 2800/122* (2013.01)

(58) Field of Classification Search
None
See application file for complete search history.

(56) References Cited

U.S. PATENT DOCUMENTS 7,498,038 B2 * 3/2009 Strong ........................ 424/275.1
8,551,501 B2 * 10/2013 Strong ........................ 424/275.1

OTHER PUBLICATIONS

Mora-Montes et al. 'Recognition and Blocking of Innate Immunity Cells by *Candida albicans* Chitin.' Infect Immun. May;79(5):1961-70, 2011.*

Article "Immunological Effects and Membrane Interactions of Chitosan Nanoparticles", Aditya Pattani, Vandana B. Patravale, Lata Panicker and Pravin D. Potdar, Molecular Pharmaceutics, vol. 6, No. 2, p. 345-352, 2009.
Article "Alveolar Macrophage Priming by Intravenous Administration of Chitin Particles, Polymers of N-Acetyle-D-Glucosamine, in Mice", Yoshimi Shibata, L. Ann Foster, W. James Metzger and Quentin N. Myrvik, Infection and Immunity, May 1977, vol. 65, No. 5, pp. 1734-1741.
Article, The Chitin Connection, David L. Goldman and Alfin G. Vicencio, mbio.asm.org, Mar./Apr. 2012, vol. 3, Issue 2, e00056-12.
Article, Induction of proinflammatory mediators by CHI3LI is reduced by chitin treatment: decreased tumor metastasis in a breast cancer model, Stephania Libreros, Ramon Garcia-Areas, Yoshimi Shibata, Roberto Carrio, Marta Torroella-Kouri and Vijaya Iragavarapu-Charyulu, International Journal of Cancer, 131, 377-386 (2012).
Article, Oral Administration of Chitin Down-Regulates Serum IgE Levels and Lung Eosinophilia in the Allergic Mouse, Yoshimi Shibata, L. Ann Foster, John F. Bradfield and Quentin N. Myrvik, J Immunol 2000, 164:1314-3121.
Article, Immunoregulatory Roles of IL-10 in Innate Immunity: IL-10 Inhibits Macrophage Production of IFN-γ-Inducing Factors but Enhances NK Cell Production of IFN-γ1, Yoshimi Shibata, L. Ann Foster, Masashi Kurimoto, Haruki Okamura, Reiko M. Nakamura, Katsuhide Kawajiri, J. Paul Justice, Michael R. Van Scott, Quentin N. Myrvik and W. James Metzger, The Journal of Immunology, 1998, 161: 4283-4288.

* cited by examiner

*Primary Examiner* — Nora Rooney
(74) *Attorney, Agent, or Firm* — The Weintraub Group, P.L.C.

(57) ABSTRACT

A method of diagnosing allergic asthma in patients, including the steps of: obtaining from a subject a first sample of peripheral blood immune cells and a second sample of peripheral blood immune cells; adding chitin to the first sample; measuring the average amount of IFN-γ in both the first sample and the second sample to get a first value and a second value respectively; and dividing the first value with the second value to get a ratio, wherein if the ratio is smaller than a threshold value, the subject is diagnosed as an allergic asthma patient.

5 Claims, 7 Drawing Sheets

CHITIN-INDUCED IMMUNE RESPONSE BASED METHOD FOR DIAGNOSING ALLERGIC ASTHMA IN PATIENTS

BACKGROUND OF THE INVENTION

1. Field of the Invention

The present invention relates to a method of diagnosing allergic asthma in patients, and more particularly to a method of diagnosing allergic asthma in patients by measuring a chitin-induced response of peripheral blood immune cells obtained from the patients.

2. Description of the Related Art

To describe the related art of the present invention, definitions and characteristics of hypersensitivity, asthma and chitin have to be addressed first.

Hypersensitivity is an inflammatory reaction induced by body fluid or cell mediator from immune system, which may lead to tissue damage or even death. These reactions can be grouped into four types according to their induction mechanisms. Each type has its unique functional molecules and clinic characteristics. In clinic, most common allergic diseases including asthma, allergic rhinitis, and hay fever exhibit type I hypersensitivity.

Type I hypersensitivity is induced by allergens which might be protein or small molecule chemicals (Roitt et al., 1998). Type I hypersensitivity is a quick response with allergy reactions appearing in several minutes right after an allergen exposure. In general, these reactions have two phases—phase I in an early period of sensitization and phase II in a prolonged period after phase I. When an individual is exposed to certain allergen, his/her plasma cells will produce antibodies, especially IgEs, to fight against it. This kind of antibody has high affinity against FcεRI receptor on the surface of tissue mast cell and basophil, and low affinity against IgE receptor (FcεRII or CD23) on the surface of lymphocyte, eosinophil, platelet, and macrophage. When IgEs are bound to Fc receptors on the surfaces of mast cells or basophils, the sensitization is set out. If the individual is exposed to the same allergen again, (phase II of type I reaction), the allergen will be bound to IgE on cell receptor, causing degranulation of mast cell or basophil and release of vascular activating substance such as fast-responded histamine in huge quantity. Histamine is the major component in granules of mast cell, possessing up to 10% of granule weight. It causes smooth muscle contraction, mucus secretion increase, vessel expansion and permeability increase. Besides histamine, mast cell granule contains serotonin which causes smooth muscle contraction, increases respiration rate, facilitates histamine release and leads to overall severe allergic symptoms [Peters et al., 1998].

Asthma, one of the most common allergic diseases, is a chronic airway inflammatory disease along with major symptoms of shortness of breath, wheezing, chest tightness, and slow cough. These symptoms may last very long period of time. Most patients can recover from the disease as well as keep the disease under control to lead a normal life. Generally speaking, the cause of asthma is very complicated due to the interaction between genetic and environmental stimulation factors. For many patients, this disease might root from their infant stage. Therefore, genetic and environmental factors play important roles of establishment and development of asthma. In clinic, it is grouped as extrinsic and intrinsic asthma according to the cause of asthma. Extrinsic asthma is a type of allergic and immunogenic asthma induced by allergens from air or blood, which can be dust mite, pollen, perfume or viral antigen. Intrinsic asthma is a type of primary and non-allergic asthma caused by chronic and secondary obstructive bronchitis, which is not correlated to allergen [Kay, Trends Mol. Med. 2005; 11(4):148-152].

Chitin is the second abundant natural polymer next to cellulose. It is widely distributed in cell wall of algae and mushroom [Bulawa, 1993], and the shell of shrimp, crab and insect [Neville et al., 1976]. Chitin is a cellulose-like high molecular weight polymer. This unbranched polysaccharide polymer is formed by linking N-acetyl glucosamine and glucosamine through β-(1,4) glycosidic bond [Tharanathan and Kittur, 2003]. Due to its own highly compact crystal structure, extrinsic and intrinsic hydrogen bonds are formed in molecular level, resulting in low water solubility. Also, the sturdy hydrogen bond structure enables chitin to be physically and chemically more stable than other polysaccharide and not easy to break or distort under natural conditions [Merzendorfer and Zimoch, 2003].

Recently, due to massive supply of natural polymer, chitin is applied in all areas along with discoveries of lots of biomedical characteristics. It includes (1) non-toxicity and no obvious side effect to animal [Minami Saburo et al., 2002]; (2) bioactivity through forming micelles by absorbing food lipid in intestine to reduce micelle uptake, lower triacylglycerol and cholesterol in blood [Zacour et al., 1992], further relieve obesity, and prevent heart disease. Besides, chitin can attract negative charged chloride ion from salt and remove it out of the body for effective prevention of high blood pressure [Zacour et al., 1992]; (3) liver protection. Theoretically, chitin is believed to protect liver, inhibit tumor establishment and growth, treat stomach canker, control blood pressure, and boost immune system [Esteban et al., 2000]; and (4) high bio-compatibility, which will not induce antibody. Therefore, chitin and its derivatives are widely used in all areas, including medical, chemical engineering, agriculture, food processing and etc. [Tharanathan and Kittur, 2003; Synowiecki and Al-Khateeb, 2003; Khor and Lim, 2003].

Recent studies show that chitin can improve animal immunity, help inhibit tumor growth and protect host from pathogen infection [Murata et al., 1991 Nishimura et al., 1985], wherein 30% or 70% deacetylated chitin and carboxymethylchitin are the most effective material for inducing macrophage cytotoxicity to inhibit tumor growth [Nishimura et al., 1984 Nishimura et al., 1985]. Also, chitin which has been injected to guinea pig can activate C3 and C5 complement proteins therein to increase to the similar level by zymosan [Tokura et al., 1999]. Besides, other study also shows that chitin can significantly elevate macrophage secreted NO, enhancing anti-pathogen and tumor ability [Peluso et al., 1994]. Therefore chitin and chitin polysaccharide are believed to be capable of improving non-specific immune response, such as macrophage proliferation promotion, nitrogen compound secretion, and anti-bacterial and anti-tumor ability elevation.

Besides, Shibata et al. show that chitin can improve TH1 immunity against antigen Mycobacterium [Shibata et al., Infect Immune, 2001 69(10) 6123-6130]. When Mycobacterium protein (MPB-59) is used alone to immunize rat, TH2 response can be induced with the characteristics as increase of total amount of IgEs and specific IgG1s in serum. Besides, TH2 cells will produce IL-4, IL-5 and IL-10. Spleen TH1 cells produced interferon-gamma (IFNγ) and specific serum IgG2a are not detectable. If chitin is combined with MPB-50 to immune guinea pig, it shows weak TH2 response along with elevated spleen TH1 response and serum IgG2a. Therefore, chitin can improve specific immune response, promote antibody production and facilitate T cell response.

Furthermore, Shibata et al. found that chitin can significantly induce secretion of IFN-γ from TH1 cells to increase macrophage activity [Shibata et al., J Immunol, 1997 155(5) 2462-2467]. Engulfing non-allergenic chitin microparticle by macrophage leads to TH1 related cytokine production such as IL-12, IL-18 and TNF-α [Shibata et al., J Immunol, 1997 155(5) 2462-2467]. It can further activate TH1 cells or natural killer cells (NK cells) to produce IFN-γ, inhibit TH2 response, redirect the whole immune response to TH1 with effective decrease of serum IgEs and eosinophiles in lung [Shibata et al., J Immunol, 2000 164(3) 1314-1321], and finally relieve allergic symptoms. Similar results show that this type of treatment can improve airway pathological response [Musumeci et al., 2008].

Current known allergic asthma induced inflammation is highly related to allergen induced TH2 cell immune response. Therefore, chitin induced IFN-γ can be used to inhibit TH2 response in ovalbumin (OVA) sensitized asthma guinea pig and treat animal's pathological symptoms. In studying the mechanism of chitin cured ovalbumin sensitized guinea pig, it is found chitin can hardly induce sensitized or treated guinea pig immune cells to significantly produce IFN-γ, far different from the chitin-induced response of a normal guinea pig. However, this trait has not been utilized in prior art to diagnose allergic asthma in patients.

SUMMARY OF THE INVENTION

The primary objective of the present invention is to propose a fast and convenient method of diagnosing allergic asthma in patients.

Another objective of the present invention is to propose a method of diagnosing allergic asthma by processing two samples of peripheral blood immune cells obtained from a subject.

To achieve the foregoing objectives of the present invention, a novel method of diagnosing allergic asthma in patients is proposed, the method including the steps of: obtaining from a subject a first sample of peripheral blood immune cells and a second sample of peripheral blood immune cells; adding chitin to the first sample; measuring the average amount of IFN-γ in both the first sample and the second sample to get a first value and a second value respectively; and dividing the first value with the second value to get a ratio, wherein if the ratio is smaller than a threshold value, the subject is diagnosed as an allergic asthma patient.

To make it easier for our examiner to understand the objective of the invention, its structure, innovative features, and performance, we use a preferred embodiment together with the accompanying drawings for the detailed description of the invention.

DETAILED DESCRIPTION OF THE PREFERRED EMBODIMENTS

The present invention will be described in more detail hereinafter with reference to the accompanying drawings that show the preferred embodiment of the invention. To better understand the principle of the present invention, characteristics of TH1 and TH2 pathways, as well as T cell response related transcription factor should be addressed first. PS TH1 and TH2 Pathways:

Under normal condition, the status of in vivo TH1 and TH2 cell is balanced. TH1 subgroup mainly secrets IFN-γ, TNF-β and IL-2, and TH2 subgroup produces cytokines as IL-4, IL-5, IL-6, IL-10 and IL-13 [Romagnani et al., 1997]. TH1 cell is mainly involved in cellular immune response, and the cytokine it generated can activate cytotoxicity, inflammatory reaction and delayed allergic response. TH2 is involved in antibody production which can effectively induce B cell proliferation and antibody production (such as IgE) against dissociated microorganism. TH2 cell generated cytokine is related to allergic response regulation [Romagnani, 1994]. Various cytokine inductions can specifically affect T-helper cell differentiation, whereas gene transcription factor also has cellular specificity. It is known that TH1 and TH2 cell developments require STAT-1 and STAT-6, respectively [Grogan et al., Curr Opin Immunol, 2002 14(3) 366-72]. Besides, transcription factors have been found selectively expressed in TH1 and TH2 cells, such as GATA-3 in TH2 cell and T-bet in TH1 cell [Grogan et al., Curr Opin Immunol, 2002 14(3) 366-72].

In general, allergic inflammatory reaction of asthma is related to an imbalance between TH1 and TH2 cells, especially to TH2 cell generated IL-4 and IL-13 [Dittrich et al., 1997]. Due to the inhibition ability of IFN-γ on IgE synthesis and TH2 cell differentiation, lack of IFN-γ facilitates allergic inflammatory reaction. TH2 cell generated cytokine IL-4 can significantly induce B cell secreted IgE [Gascan et al., 1991] as well as inhibit macrophage activity, block IFN-γ activated macrophage effect, and induce mast cell growth and development. Furthermore, IL-5 can induce eosinophil growth and differentiation. Therefore, it is considered as a major player of allergic reaction [Robinson et al., N Engl J Med, 1992 326(5) 298-304].

Also, it is believed that asthma is a chronic airway inflammatory disease related to over Th2 immune reaction. Mass expression of cytokine as IL-4, IL-5 and IL-13 induces eosinophil and mast cell accumulation and activation, leads to chronic lung inflammation, results in airway hyperresponsiveness (AHR), and causes airway block, mucus accumulation and airway inflammation [WillsKarp et al., Science, 1998; 282(5397): 2258-2261]. Although high level of IL-4, IL-5 and IL-13 inducing over Th2 immune response is related to allergic diseases, more and more evidences demonstrate low Th1 immune response is also the cause of these allergic diseases. T cell response related transcription factor:

Premature helper T cell differentiation is affected by different cytokine stimulation, different transcription factor, or the interaction between cytokine and transcription factor. For example: the presence of IL-4 can stimulate cell differentiation towards type II helper T cell, and the presence of IL-12 can stimulate cell differentiation towards type I helper T cell [Szabo et al., Science, 295(5553):338-42]. Based on this molecular biology knowledge, some transcription factors are chosen as experimental material in the present invention:

1. GATA-3: a specific transcription factor for type II helper T cell. Started by IL-4 gene transcription, it promotes undifferentiated helper T cell differentiation towards type II helper T cell. Besides, GATA-3 can inhibit IL-12 to block type I helper T cell development [Thomas et al., 2001].

2. T-bet It is a specific transcription factor for type I helper T cell, which can promote undifferentiated helper T cell to differentiate. IL-12 induced IFN-γ can promote T-bet gene expression, and T-bet can also increase IFN-γ production in a mutual positive feedback relationship [Szabo et al., Science, 295(5553):338-42].

The present invention has used chitin to induce peripheral blood mononuclear cells of allergic asthma patient and normal healthy person to produce IFN-γ, and observed the difference of their immune response. The experiment result shows that chitin induced IFN-γ concentration of peripheral blood mononuclear cells from allergic asthma patients is significantly lower than that from healthy normal persons. Regarding the correlation between IFN-γ production ratio and allergen hypersensitivity of allergic asthma patient, the results show patient highly allergic to dust mite has lower IFN-γ production ratio whereas patient less allergic to dust mite has higher IFN-γ production ratio. Therefore, low immune response of asthma patient against chitin might be partially correlated to patient's specific IgE against to dust mite. Although dust mite is full of chitin, it might be correlated with specific IgE concentration and chitin induced IFN-γ. However, chitin is also found in crab and shrimp shell with less correlation between hypersensitivity of patient and chitin induction.

As such, the present invention discloses a method of diagnosing allergic asthma in patients, the method including the steps of: obtaining from a subject a first sample of peripheral blood immune cells and a second sample of peripheral blood immune cells; adding chitin to the first sample; measuring the average amount of IFN-γ in both the first sample and the second sample to get a first value and a second value respectively; and dividing the first value with the second value to get a ratio, wherein if the ratio is smaller than a threshold value, the subject is diagnosed as an allergic asthma patient.

A preferred embodiment of the present invention is that immune cell is mononuclear cell. ELISA is used for IFN-γ quantification. IFN-γ production ratio equals to ELISA standard curve derived average of chitin-induced IFN-γ concentration from each sample divided by that of blank assay.

The method of the present invention can also be used for diagnosing healthy person without allergic asthma. When IFN-γ production ratio is over 10, the subject is diagnosed as a healthy person without allergic asthma. When IFN-γ production ratio is between 6-10, the subject is diagnosed as a suspected allergic asthma patient.

The method of present invention can also be used for diagnosing severe dust mite hypersensitive patient. When IFN-γ is lower than IFN-γ production ratio of 2, the subject is diagnosed as severe dust mite hypersensitive patient.

EXAMPLE

Example 1

The present invention collected data from 30 allergic asthma patients and 30 non-patients for this study. The criteria of selected patients were first-visit allergic asthma patients (experimental group) and non-allergic asthma history healthy persons (control group). Elimination criteria were patients with hypersensitivity history. Below are allergen test results over allergic asthma patients.

Total IgE concentration of allergic asthma patients:

| Patient number | Total IgE (mg/dl) |
| --- | --- |
| 1 | 1873 |
| 2 | 60.2 |
| 3 | 104 |
| 4 | 11.4 |
| 5 | 167 |
| 6 | 79.3 |
| 7 | 193 |
| 8 | 61.8 |
| 9 | 695 |
| 10 | 207 |
| 11 | 64.1 |

The hypersensitivity level against allergen of allergic asthma patients (Table I):

| Patient | D. pteronyssinus | D. farinae | Cockroach | Egg white | Crab | Shrimp | Dog dander |
| --- | --- | --- | --- | --- | --- | --- | --- |
| 1 | 6 | 6 | 0 | 1 | 0 | 0 | 2 |
| 2 | 2 | 2 | 0 | 0 | 0 | 0 | 0 |
| 3 | 0 | 0 | 0 | 0 | 0 | 0 | 0 |
| 4 | 0 | 0 | 0 | | | | 0 |
| 5 | 2 | 2 | 0 | | | | 0 |
| 6 | 4 | 3 | 0 | 0 | 0 | 0 | 0 |
| 7 | 3 | 2 | 2 | 1 | 2 | 2 | 1 |
| 8 | 2 | 2 | 0 | | | | 0 |
| 9 | | | | 0 | 1 | 1 | |
| 10 | 4 | 4 | 0 | | | | 0 |
| 11 | 1 | 0 | 0 | 1 | 0 | 0 | 0 |

The hypersensitivity level against allergen of allergic asthma patients (Table II):

| Patient | Cat dander | Candida albicans | Milk | Fish (cod) | Peanut |
|---|---|---|---|---|---|
| 1 | 0 | 0 | 0 | 0 | 0 |
| 2 | 0 | 1 | 0 | 0 | 0 |
| 3 | 0 | 0 | 0 | 0 | 0 |
| 4 | 0 | 0 | | | |
| 5 | 0 | 0 | | | |
| 6 | 0 | 0 | 0 | 0 | 0 |
| 7 | 0 | 0 | 2 | 0 | 0 |
| 8 | 1 | 0 | | | |
| 9 | | | 0 | 0 | 0 |
| 10 | 0 | 0 | | | |
| 11 | 0 | 0 | 0 | 0 | 0 |

Chitin Preparation

After the allergen test was done, chitin micro particles (4-5 μm in diameter) were provided and examined by Dr. Chen Jeen-Kuan from CPC Biotech RD department. Endotoxin-free verified microchitin was prepared as 10 mg/ml suspension in phosphate buffered saline (PBS). It was stored at 4 after autoclaving and mixed well before use.

Isolation of Peripheral Blood Mononuclear Cells

Heparin tube (Na-Heparin) was used for blood collection from healthy persons and allergic asthma patients. After centrifugation, removed upper layer plasma and froze it at −80 for later use. Residual blood was mixed with PBS, and moved to a centrifugation tube with Ficoll. After another centrifugation, there should be three layers based on Ficoll concentration gradient. The middle white-cloudy layer contained human peripheral mononuclear cells (PBMC). PBMC was isolated, washed with PBS for 2~3 times, and kept on ice.

Cell Culture

After separation of PBMC, cells cultured in 96 well plates with complete medium of dissolved RPMI 1640, 10% fetal bovine serum (FBS), 1% L-Glutamine and 2% Penicillin and Streptomycin. 200 μl/well medium was added in 96 well dishes or 2 ml medium in 24 well dishes. The cell number in each well is $2 \times 10^5$ (for 96 well dishes) or $2 \times 10^6$ (for 24 well dishes). Different stimulants were added into each sample to culture it for appropriate time. Plates were placed in an incubator to culture cells at 37 with 5% $CO_2$.

Sample Preparation (Cell Culture Supernatant and Cell)

Cell culture plates were placed into an incubator, taken out at day 5, and then put into an eppendorf. After centrifugation, cell pellets appeared in the bottom of the eppendorf. Supernatant was removed into a new tube which was then labeled before frozen at −80 for further ELISA test.

Enzyme-Linked Immuno-Sorbent Assay (ELISA)

ELISA was used to determine IFN-γ concentration. Anti-human cytokine capture antibody was diluted in 250 fold with coating buffer and add 100 μl/well to coat 96-well ELISA plate overnight at 4. The plate was washed with washing buffer (0.05% Tween-20 PBS) for several times (as manufacturer's instruction). 200 μl of assay diluent was added to each well to block non-specific spaces for 1 hour at room temperature. The plate was washed with washing buffer for several times. 100 μl/well of 2 fold diluted standard (maximal starting concentration of 2000 pg/ml IFN-γ) was added in duplicate for 2 hours at room temperature. The plate was washed with washing buffer for several times. 100 μl/well of detection antibody (250 fold diluted with assay diluent) was added and incubated for 1 hour at room temperature. The plate was washed with washing buffer for several times. Avidin-horseradish peroxidase (Avidin-HRP) was added and incubated for 30 minutes at room temperature. Finally, the plate was washed with washing buffer for several times and 100 μl/well of substrate (tetramethylbenzidine-TMB) was added for 15-minute reaction. 50 μl/well of 2N H2SO4 was added to stop the reaction. OD450 nm was determined by ELISA reader.

Example 2

Microchitin-induced IFN-γ Production from Peripheral Blood Mononuclear Cells

Figure 1:
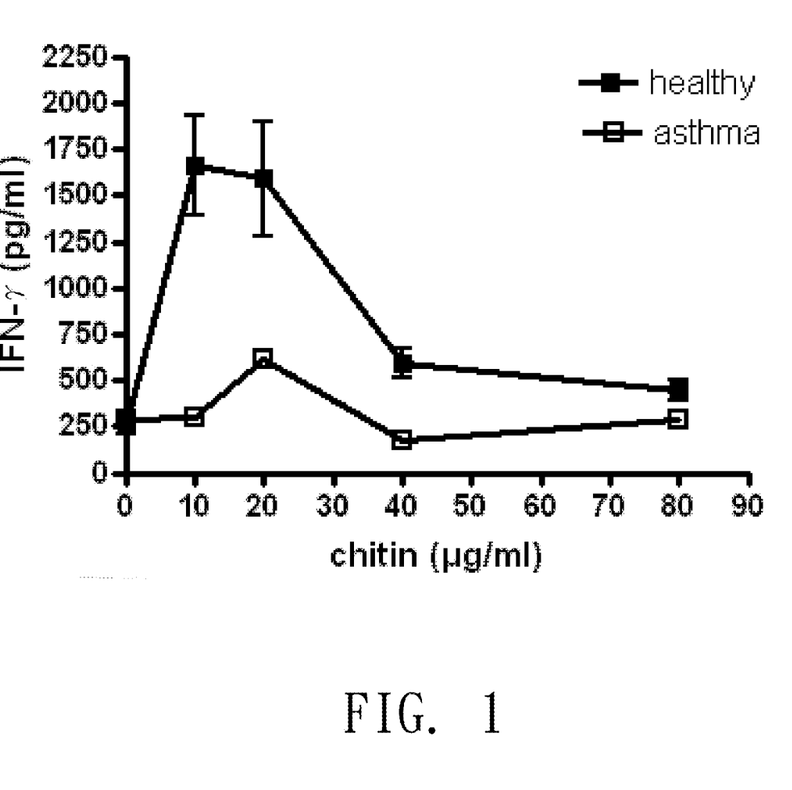
FIG. 1 shows two concentration profiles of IFN-γ produced by retrieved peripheral blood mononuclear cells (PBMC) in response to chitin over a range of doses for a group of healthy subjects and a group of asthma subjects respectively.
Figure 2:
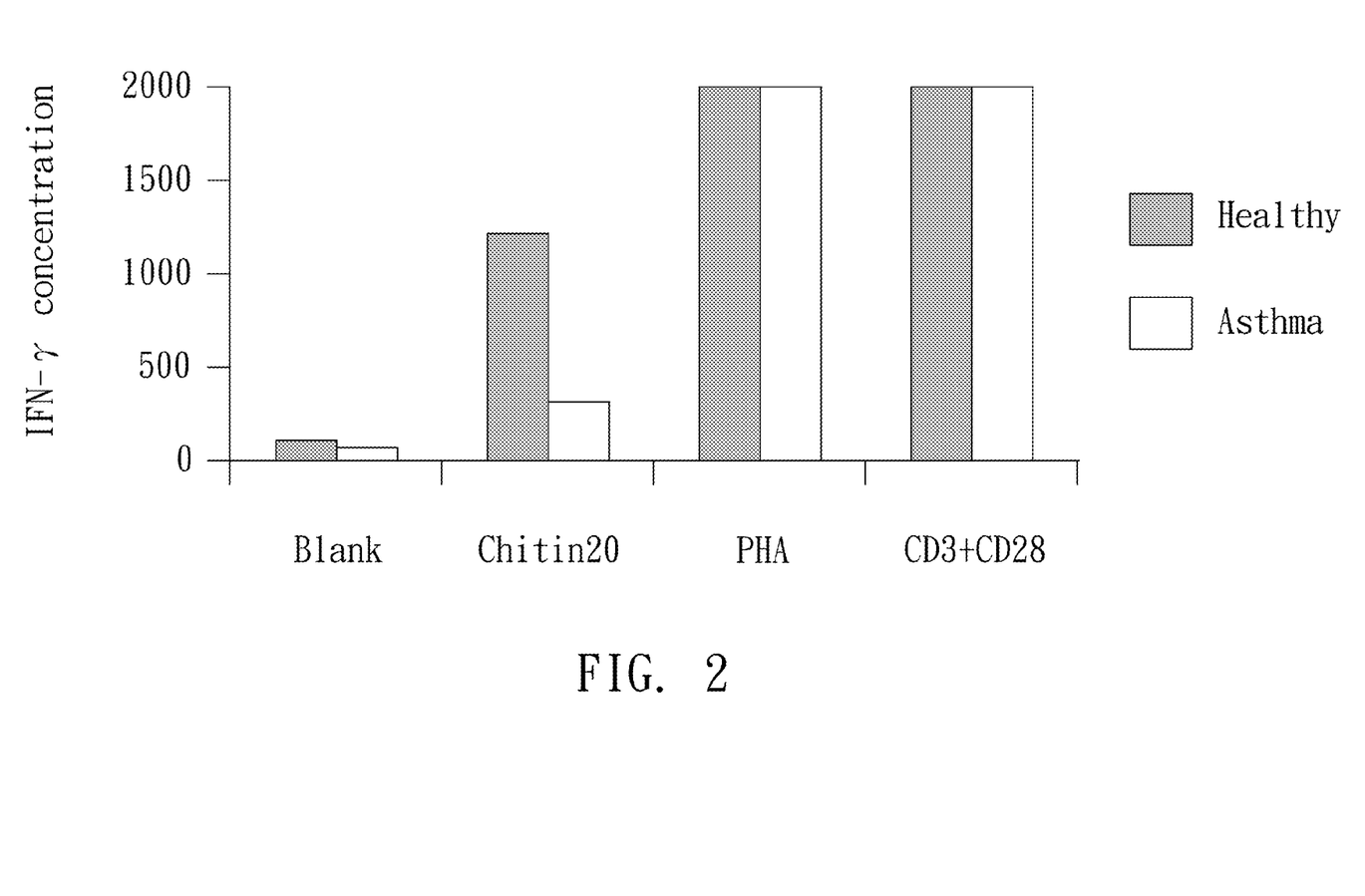
FIG. 2 shows comparison of IFN-γ concentrations produced by retrieved peripheral blood mononuclear cells (PBMC) in response to different stimulants for a group of healthy subjects and that for a group of asthma subjects.

To confirm whether microchitin can induce IFN-γ production, the present invention co-cultured various concentrations of chitin (5 10 20 40 80 μg/ml) with peripheral blood mononuclear cells from normal healthy persons, and determined IFN-γ production at various time points (from day 4 to day 7). PBMC were freshly obtained from healthy individuals or asthma patients, and stimulated with 20 μg/ml of chitin. Stimulant-free (blank) was served as a control. After 5 days of culture, the culture supernatant was harvested and the presence of IFN-γ was quantified by ELISA. The representative results are shown in FIG. 1. IFN-γ production of peripheral blood mononuclear cells can be induced by various concentrations of chitin. Chitin concentration of 20 μg/ml had the most optimal response, such as 1072.2, 1897.4, 2687.1, and 4708.6 pg/ml of IFN-γ production at day 4, 5, 6, and 7, respectively. The concentration of released IFN-γ was elevated according to the reaction time under same concentration of chitin induction. As shown in FIG. 2, in order to compare IFN-γ production by PBMC from healthy individuals and asthma patients in response to different stimulants, PBMC were freshly obtained from healthy individuals and asthma patients, and stimulated with chitin, phytohemagglutinin (PHA) and anti-CD3 plus anti-CD28. Stimulant-free (blank) was served as a control. After desired culture days (2 days for PHA, 3 days for anti-CD3 plus anti-CD28, and 5 days for chitin), the culture supernatant was harvested and the presence of IFN-γ was quantified by ELISA.

Example 3

The Difference of Peripheral Blood Mononuclear Cell Expressed IFN-γ Between Asthma Patients and Healthy Persons In order to compare the difference of peripheral blood mononuclear cell expressed IFN-γ between asthma patients and healthy persons, ELISA was used to measure the concentration of IFN-γ from supernatant of co-cultured peripheral blood mononuclear cells and microchitin. The chitin-induced IFN-γ production ratio was calculated by dividing the average of chitin-induced IFN-γ concentration (in duplicate) with that of blank. Blank was obtained in the cell culture without chitin treatment.

Figure 3:
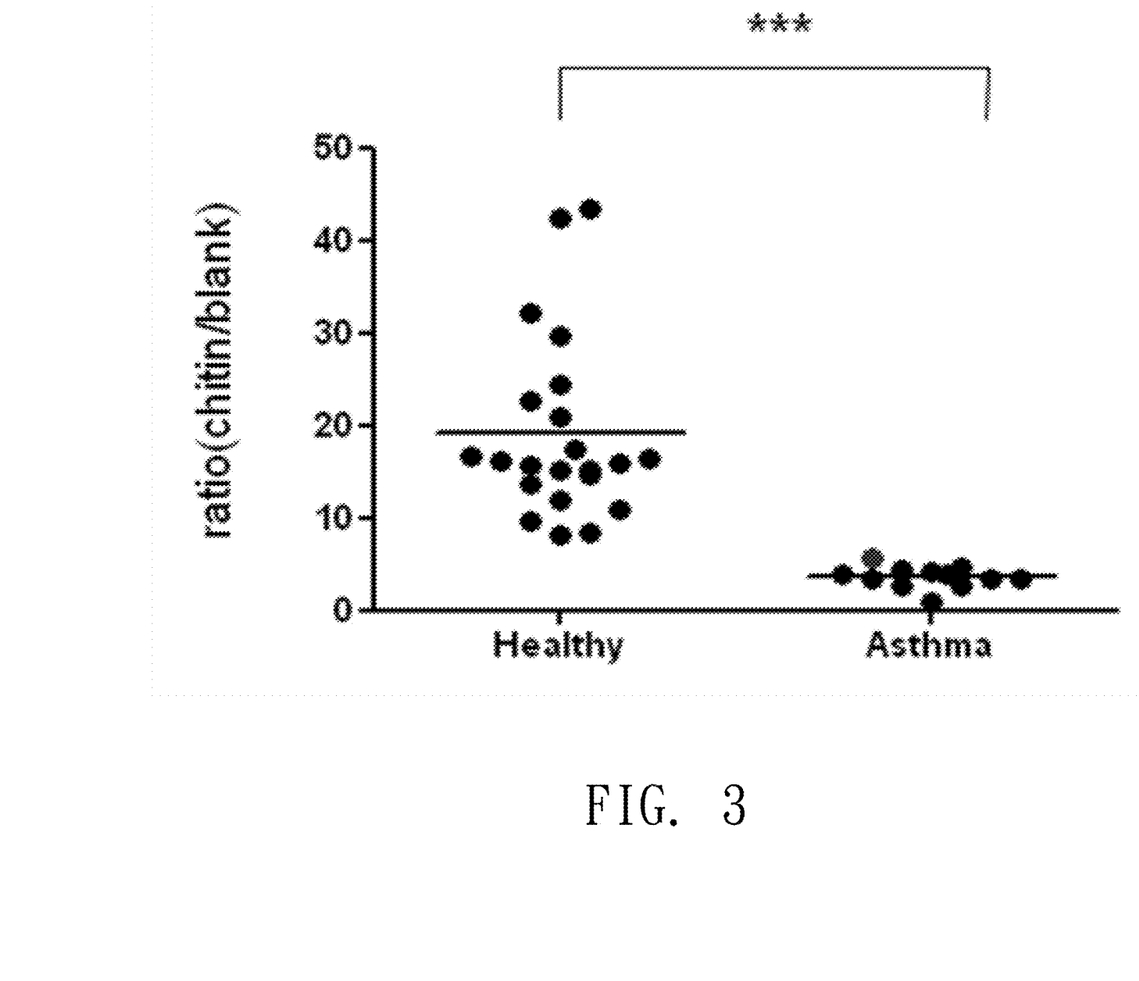
FIG. 3 shows comparison of IFN-γ production by peripheral blood mononuclear cells (PBMC) from healthy subjects and asthma subjects in response to chitin. The ratio (chitin/blank) is derived by dividing chitin stimulated IFN-γ concentration with chitin-free IFN-γ concentration. The mean and individual results by PBMC from healthy subjects (n=24) and asthma subjects (n=12) are shown after an unpaired Student T test, with *** representing p<0.001.

There were 24 healthy subjects as shown in FIG. 3. PBMC were freshly obtained from healthy individuals or asthma patients, and stimulated with 20 μg/ml of chitin. Stimulant-free (blank) was served as a control. After 5 days of culture, the culture supernatant was harvested and the presence of IFN-γ was quantified by ELISA. Most IFN-γ production ratio was between 15~25, with exception of 40 and above, one below 10, and most over 10. However, the IFN-γ production ratio of 12 samples from asthma patients was between 4-6, with average of 5, and some samples less than 2. After that, analyzed data from asthma patient and healthy persons by nonparametric Mann-Whitney U test or student t-test, the a value of two-tailed test was below 0.001 and p was less than 0.001 showing statistically difference. The average ratio of healthy person was 20 and that of asthma patient was 4 with p value of 0.0008 which was less than set α value of 0.001. Therefore, this result shows statistical difference.

Figure 4:
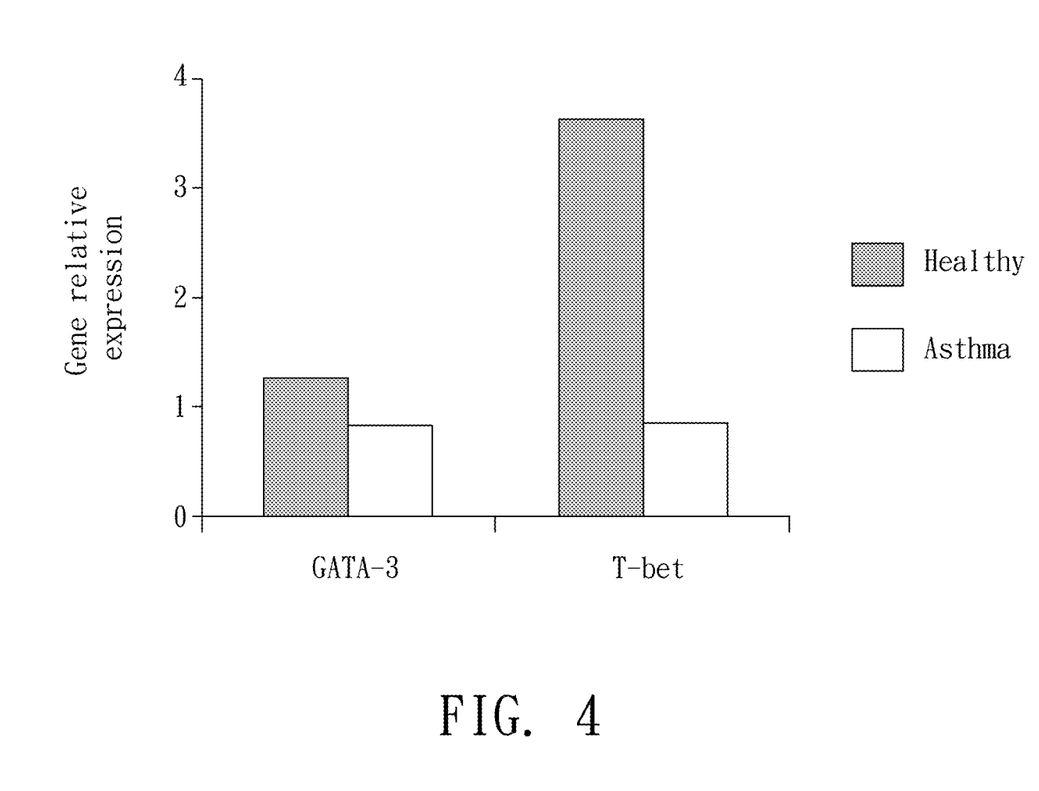
FIG. 4 shows the gene relative expressions of transcription factors, GATA-3 and T-bet, in chitin stimulated PBMC analyzed by real-time PCR (Polymerase Chain Reaction). The gene relative expression is a ratio of an averaged chitin stimulated transcription factor expression over an averaged chitin-free (blank) transcription factor expression.

To understand the expression of transcription factors, GATA-3 and T-bet, in chitin stimulated PBMC, PBMC were freshly obtained from healthy individuals and asthma patients, and stimulated with 20 μg/ml of chitin. Stimulant-free (blank) was served as a control. After 5 days of culture, the cells were harvested and analyzed for the expression of transcription factors, GATA-3 and T-bet by real-time RT-PCR. Data are shown in FIG. 4.

From results above, microchitin induced IFN-γ production from peripheral blood mononuclear cells was significantly different between asthma patients and healthy persons.

Example 4

Figure 5:
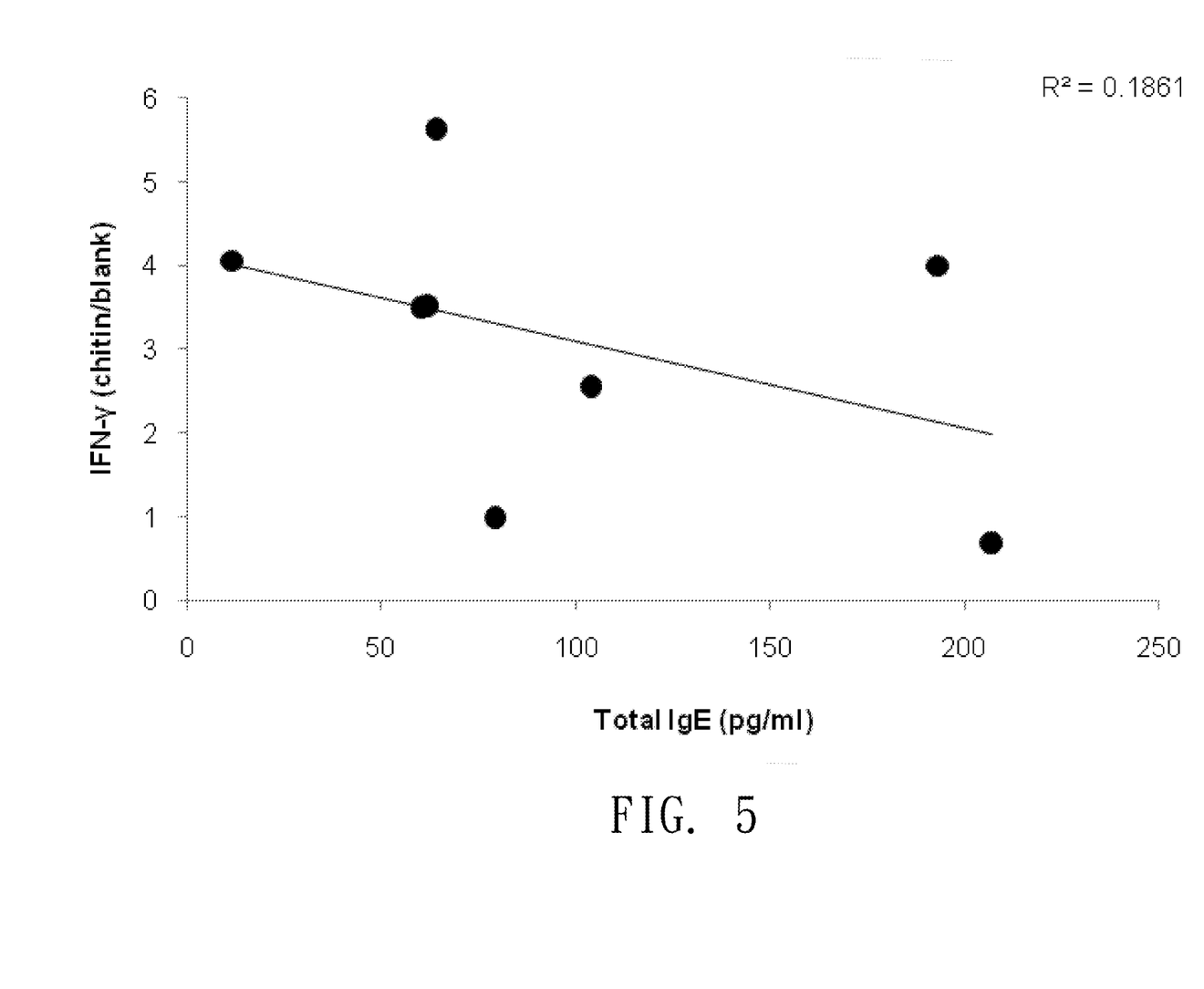
FIG. 5 shows the correlation between chitin stimulated IFN-γ production and serum total IgE in asthma patients. The IFN-γ (chitin/blank) is derived by dividing chitin stimulated IFN-γ concentration with chitin-free IFN-γ concentration and correlated with the clinical results for serum total IgE concentration in asthma subjects (n=8, $R^2$=0.1861).

Correlation of Asthma Patient's Low Reactivity Against Chitin and Allergic Diseases After that, it came the allergen specific IgE. As shown in FIG. 5, to understand the correlation of chitin stimulated IFN-γ production with serum total IgE in asthma patients, PBMC were freshly obtained from healthy individuals and asthma patients, and stimulated with 20 μg/ml of chitin. Stimulant-free (blank) was served as a control. After 5 days of culture, the culture supernatant was harvested and the presence of IFN-γ was quantified by ELISA. Data presented here are the ratio of chitin stimulated IFN-γ production levels divided by blank and correlated with the clinical results for serum total IgE levels in asthma patients (n=8).

Figure 6:
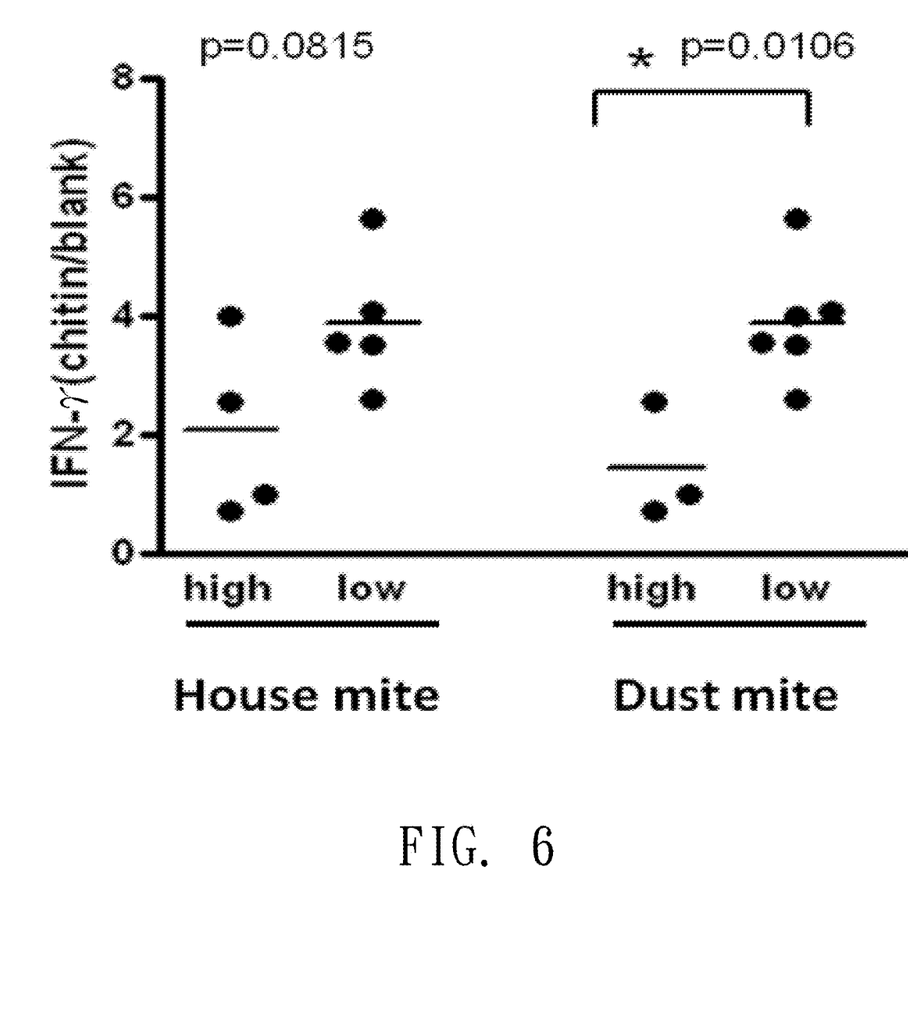
FIG. 6 shows the correlation between IFN-γ production and hypersensitivity level against mite for asthma subjects. The hypersensitivity level against mite for asthma subjects is grouped as high hypersensitivity (concentration of specific IgE against mite 1.0 mg/dl) and low hypersensitivity (10.0 mg/dl). For the correlation result against house mite, p=0.0815, for the correlation result against dust mite, p=0.0106, and the results were obtained by student t test.
Figure 7:
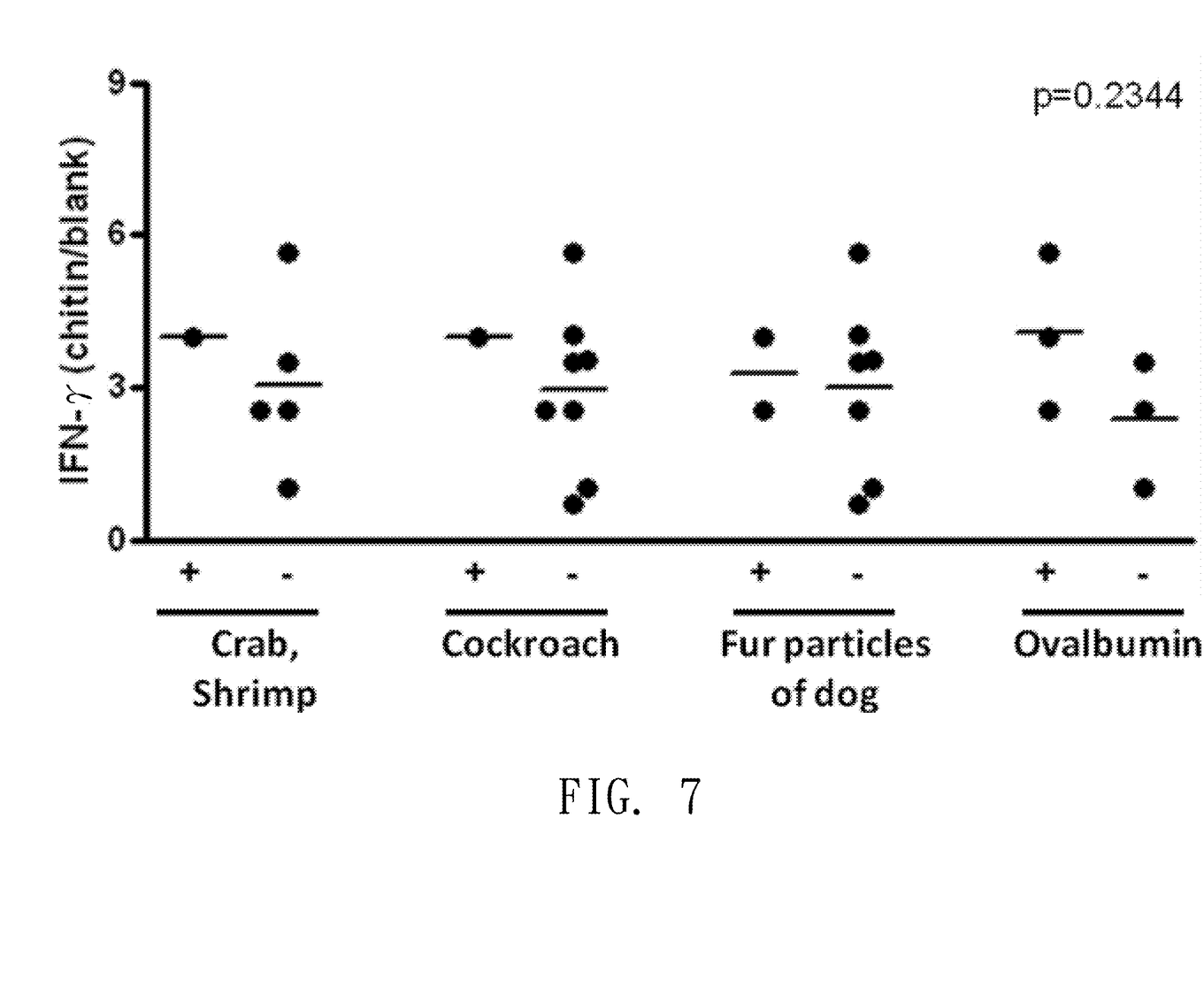
FIG. 7 shows the correlation between IFN-γ production and severity of allergic response against common allergens for asthma patients. Patients are grouped as allergic (specific IgE against allergen 1.0 mg/dl) and non-allergic (1.0 mg/dl) based on the level of hypersensitivity against common allergens. The correlation between IFN-γ production ratio and allergic/non-allergic for patients against the listed allergens were performed by student t test and p=0.2344.

However, mite was the top allergen in Taiwan of 90.79% responsible for inducing child allergic asthma. Mite can be grouped as house dust mite and dust mite. Therefore, the present invention compared asthma patient's allergic response against house dust mite and dust mite (dust mite specific IgE concentration) and IFN-γ production ratio. As shown in FIG. 6, the present invention observed that patients highly allergic to mites have lower IFN-γ production ratio, whereas patients less allergic to mites have higher IFN-γ production ratio, and the statistic difference is especially obvious for dust mite (p=0.0106). The present invention demonstrated the weak immune response of asthma patients against chitin might be partially correlated to their specific IgE against dust mite. Besides, the present invention also compared patient's response against other allergen (crab, shrimp, dog dander, cockroach and egg white) with IFN-γ production ratio. It demonstrates no correlation as shown in FIG. 7.

In conclusion, the current invention provides a novel method of diagnosing allergic asthma in patients.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance than the conventional structure and further complies with the patent application requirements and is submitted to the Patent and Trademark Office for review and granting of the commensurate patent rights.

What is claimed is:

1. A chitin-induced immune response based method for diagnosing allergic asthma in patients, comprising the steps of:
   (a) obtaining from a subject a first sample of peripheral blood immune cells and a second sample of peripheral blood immune cells;
   (b) mixing said first sample of peripheral blood immune cells with heparin or Na-heparin, and mixing said second sample of peripheral blood immune cells with heparin or Na-heparin;
   (c) adding a stimulant of chitin micro particles in an amount of 5-80 μg/ml, to the first sample;
   (d) performing an immunosorbent assay on the first sample and second sample;
   (e) measuring the average amount of IFN-γ in both said first sample and said second sample to get a first value and a second value, respectively;
   (f) dividing said first value with said second value to get a ratio, and
   (g) wherein if said ratio is smaller than a threshold value, said subject is diagnosed as an allergic asthma patient.

2. The chitin-induced immune response based method for diagnosing allergic asthma in patients of claim 1, wherein said peripheral blood immune cell is a mononuclear cell.

3. The chitin-induced immune response based method for diagnosing allergic asthma in patients of claim 1, wherein said measuring the average amount of IFN-γ comprises using an ELISA standard curve to derive said average amount.

4. The chitin-induced immune response based method for diagnosing allergic asthma in patients of claim 1, wherein said subject is diagnosed as healthy person without allergic asthma when said ratio is over 10.

5. The chitin-induced immune response based method for diagnosing allergic asthma in patients of claim 1, wherein, said subject is diagnosed as a suspected allergic asthma patient when said ratio is below 10.

* * * * *